(12) United States Patent
Genet et al.

(10) Patent No.: US 6,437,149 B1
(45) Date of Patent: Aug. 20, 2002

(54) CATIONIC AMINOANTHRAQUINONES, THEIR USE FOR DYEING KERATINOUS FIBERS, DYEING COMPOSITIONS CONTAINING THEM AND METHODS OF DYEING

(75) Inventors: Alain Genet, Aulnay sous Bois; Alain Lagrange, Coupvray, both of (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 09/449,539

(22) Filed: Nov. 29, 1999

(30) Foreign Application Priority Data

Nov. 30, 1998 (FR) .............................. 98 15046

(51) Int. Cl.⁷ ................ C07D 233/54; C07D 265/30; C07D 251/12; C07C 50/18
(52) U.S. Cl. .................... 548/335.1; 552/255; 544/106; 544/111; 544/180; 544/359; 546/269.7; 546/271.7
(58) Field of Search ............... 552/255; 548/335.1; 544/106, 111, 180, 359; 546/269.7, 271.7

(56) References Cited

U.S. PATENT DOCUMENTS

| | | | | |
|---|---|---|---|---|
| 2,611,772 A | * | 9/1952 | Allen et al. ................. | 260/378 |
| 3,272,792 A | * | 9/1966 | Tager et al. ................. | 260/155 |
| 3,442,895 A | | 5/1969 | Bugaut et al. ............... | 552/255 |
| 3,467,483 A | | 9/1969 | Bugaut et al. ............... | 552/255 |
| 3,528,972 A | | 9/1970 | Kalopissis et al. .......... | 552/255 |
| 3,671,529 A | * | 6/1972 | Altermatt et al. ........... | 260/294 |
| 3,997,519 A | * | 12/1976 | Armbruster ................. | 552/255 |
| 4,051,155 A | * | 9/1977 | Hoare ........................ | 260/379 |
| 4,123,222 A | * | 10/1978 | Loew ......................... | 260/378 |
| 4,296,044 A | * | 10/1981 | Duchardt et al. ............ | 260/381 |
| 4,310,666 A | * | 1/1982 | Zee-Cheng et al. ......... | 552/255 |
| 4,451,398 A | * | 5/1984 | Patsch et al. ............... | 260/157 |
| 4,540,788 A | * | 9/1985 | Murdock .................... | 546/264 |
| 4,655,970 A | * | 4/1987 | Priester et al. .............. | 260/378 |
| 4,661,293 A | * | 4/1987 | Zielske ....................... | 552/255 |
| 4,692,278 A | * | 9/1987 | Blattner et al. ............. | 552/255 |
| 4,715,993 A | * | 12/1987 | Murdock et al. ............ | 552/255 |
| 4,732,893 A | * | 3/1988 | Pasini et al. ................. | 556/117 |
| 4,894,451 A | * | 1/1990 | Krapcho et al. ............. | 552/255 |
| 4,940,692 A | * | 7/1990 | Bach et al. .................. | 552/255 |
| 5,017,713 A | * | 5/1991 | Kondo et al. ............... | 552/255 |
| 5,132,327 A | * | 7/1992 | Patterson .................... | 552/255 |
| 5,169,403 A | | 12/1992 | Chan et al. .................. | 552/255 |
| 5,204,370 A | * | 4/1993 | Jiang et al. .................. | 552/255 |
| 5,314,505 A | | 5/1994 | Chan et al. .................. | 552/255 |
| 5,486,629 A | | 1/1996 | Chan et al. .................. | 552/255 |
| 5,493,036 A | * | 2/1996 | Adam ......................... | 552/221 |
| 5,520,707 A | | 5/1996 | Lim et al. .................... | 552/255 |
| 5,733,880 A | * | 3/1998 | Mincher ...................... | 552/255 |
| 5,882,358 A | * | 3/1999 | Smith et al. ................. | 552/255 |
| 5,961,664 A | * | 10/1999 | Anderson .................... | 552/255 |

FOREIGN PATENT DOCUMENTS

| | | |
|---|---|---|
| EP | 0 818 193 | 1/1998 |
| EP | 0 852 136 | 7/1998 |
| FR | 1 379 649 | 10/1964 |
| FR | 1 391 675 | 2/1965 |
| FR | 1 401 163 | 4/1965 |
| FR | 1 422 016 | 11/1965 |
| FR | 1 430 089 | 1/1966 |
| FR | 1 584 965 | 12/1969 |
| FR | 2 050 397 | 4/1971 |
| FR | 2 548 895 | 1/1985 |
| GB | 1 205 365 | 9/1970 |

OTHER PUBLICATIONS

English language abstract of EP 0 852 136.
English language Derwent Abstract of FR 1 584 965.
English language Derwent Abstract of FR 2 050 397.
English language Derwent Abstract of FR 2 548 895.

* cited by examiner

Primary Examiner—Mukund J. Shah
Assistant Examiner—Venkataraman Balasubramanian
(74) Attorney, Agent, or Firm—Finnegan, Henderson, Farabow, Garrett & Dunner, L.L.P.

(57) ABSTRACT

Cationic aminoanthraquinones in which at least one cationic charge is delocalized on a 5-membered unsaturated polynitrogen-containing heterocycle, their use as a direct dye in dyeing compositions for keratinous materials, in particular for human keratinous fibers such as hair, dyeing compositions containing them, and dyeing methods using these compositions.

10 Claims, No Drawings

CATIONIC AMINOANTHRAQUINONES, THEIR USE FOR DYEING KERATINOUS FIBERS, DYEING COMPOSITIONS CONTAINING THEM AND METHODS OF DYEING

The present invention relates to aminoanthraquinones containing at least one cationic group chosen from aliphatic chains containing at least one cationic charge delocalized on a 5-membered unsaturated polynitrogen-containing ring, their use as a direct dye in applications for dyeing keratinous materials, such as human keratinous fibers, for example hair, and dyeing compositions containing them.

It is known to dye keratinous fibers, and in particular hair, with dyeing compositions containing direct dyes. Direct dyes are dye molecules having an affinity for keratinous fibers. The dyeing method that uses them is a so-called direct dyeing method which comprises allowing the direct dyes to act on the fibers, and subsequently rinsing the fibers.

The colors resulting therefrom are temporary or semi-permanent colors, because the nature of the interactions which link the direct dyes to the keratinous fiber, and their desorption from the surface and/or the core of the fiber are responsible for their weak dyeing power and their poor resistance to washings and perspiration.

Cationic aminoanthraquinones whose charge is localized on the nitrogen atom have already been described among the known direct dyes. Such aminoanthraquinones are described, for example, in French Patent No. 1,422,016 and its addition No. 87,902, No. 1,391,675, No. 1,401,163, No. 1,379,649, No. 1,430,089, No.1,584,965, No. 2,050,397, and No. 2,548,895, U.S. Pat. Nos. 5,169,403, 5,314,505, 5,486,629, and 5,520,707, and European Patent Nos. 818, 193 and 852,136.

However, in hair dyeing, direct dyes are being continually sought which exhibit increasingly better characteristics.

It is thus after major research studies carried out on this subject that the inventors have discovered new cationic aminoanthraquinones in which at least one cationic charge is delocalized on a five-membered unsaturated polynitrogen-containing heterocycle and contain at least one cationic group Z, Z being chosen from quaternized aliphatic chains, aliphatic chains containing at least one quaternized saturated ring, and aliphatic chains containing at least one quaternized unsaturated ring.

This new family of dyes can exhibit the very advantageous, characteristic feature of greater solubility in the dyeing media. These new dyes can also generate colors, by direct dyeing, having an intensity and a resistance to various attacks to which the hair may be subjected: light, adverse weather conditions, shampoos, and perspiration, which is substantially improved compared with that of the colors produced with known prior art cationic aminoanthraquinones.

This discovery forms the basis of the present invention.

A subject of the present invention is thus aminoanthraquinones of the formula (I):

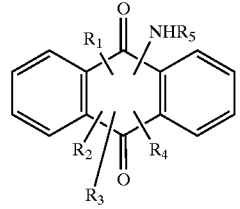

in which formula:

$R_1$, $R_2$, $R_3$ and $R_4$ which may be identical or different, are chosen from a hydrogen atom; a halogen atom; a group Z defined below; a $(C_1-C_6)$alkyl radical; a monohydroxy $(C_1-C_6$ alkyl$)$ radical; a polyhydroxy$(C_2-C_6$ alkyl$)$ radical; a cyano radical; a nitro radical; a carboxyl radical; a carbamyl radical; a sulpho radical; an unsubstituted amino radical; a substituted amino radical of formula $NHR'_5$, wherein $R'_5$ has the same meaning as $R_5$ defined below, and wherein $R'_5$ may be identical to or different from $R_5$; and an $OR_6$ and an $SR_6$ group, wherein $R_6$ is defined below;

$R_5$ is chosen from a hydrogen atom; a group Z defined below; a $C_1-C_6$ alkyl radical; a monohydroxy $(C_1-C_6$alkyl$)$ radical; a polyhydroxy$(C_2-C_6$ alkyl$)$ radical; a $(C_1-C_6)$alkoxy$(C_1-C_6$ alkyl$)$ radical; an aryl radical; a benzyl radical; a cyano$(C_1-C_6$ alkyl$)$ radical; a carbamyl$(C_1-C_6$ alkyl$)$ radical; an N-$(C_1-C_8)$ alkylcarbamyl$(C_1-C_6$ alkyl$)$ radical; an N,N-di$(C_1-C_6)$ alkylcarbamyl$(C_1-C_6$ alkyl$)$ radical; a thiocarbamyl $(C_1-C_6$ alkyl$)$ radical; a trifluoro$(C_1-C_6$ alkyl$)$ radical; a sulpho$(C_1-C_6$ alkyl$)$ radical; a $(C_1-C_6)$alkylcarboxy $(C_1-C_6$ alkyl$)$ radical; a $(C_1-C_6)$alkylsulphinyl$(C_1-C_6$ alkyl$)$ radical; an aminosulphonyl$(C_1-C_6$ alkyl$)$ radical; an N-Z-aminosulphonyl$(C_1-C_6$ alkyl$)$ radical; an N-$(C_1-C_6)$alkylaminosulphonyl$(C_1-C_6$ alkyl$)$ radical; an N,N-di$(C_1-C_6)$alkylaminosulphonyl$(C_1-C_6$ alkyl$)$ radical; a $(C_1-C_6)$alkylcarbonyl$(C_1-C_6$ alkyl$)$ radical; an amino$(C_1-C_6$ alkyl$)$ radical, wherein the alkyl portion is unsubstituted or substituted with at least one hydroxyl radical; an amino$(C_1-C_6$ alkyl$)$ radical, wherein the alkyl is substituted with at least one hydroxyl radical and wherein the amine is substituted with one or two radicals, wherein each amine radical is identical or different, and is chosen from $C_1-C_6$ alkyl, monohydroxy$(C_1-C_6$ alkyl$)$, polyhydroxy$(C_2-C_6$ alkyl$)$, $(C_1-C_6)$alkylcarbonyl, carbamyl, N-$(C_1-C_6)$alkylcarbamyl, N,N-di$(C_1-C_6)$-alkylcarbamyl, $(C_1-C_6)$alkylsulphonyl, formyl, trifluoro $(C_1-C_6)$alkylcarbonyl, $(C_1-C_6)$alkylcarboxyl, thiocarbamyl, and the group Z defined below, or may form, together with the nitrogen atom to which they are attached, a 5- or 6-membered ring containing carbon or containing at least one heteroatom;

$R_6$ is chosen from a hydrogen atom; a $C_1-C_6$ alkyl radical; a monohydroxy$(C_1-C_6$ alkyl$)$ radical; a polyhydroxy $(C_2-C_6$ alkyl$)$ radical; a group Z defined below; a $(C_1-C_6)$ alkoxy$(C_1-C_6$ alkyl$)$ radical; an aryl radical; a benzyl radical; a carboxy$(C_1-C_6$ alkyl$)$ radical; a $(C_1-C_6)$ alkylcarboxy$(C_1-C_6$ alkyl$)$ radical; a cyano$(C_1-C_6$ alkyl$)$ radical; a carbamyl$(C_1-C_6$ alkyl$)$ radical; an N-$(C_1-C_6)$ alkylcarbamyl$(C_1-C_6$ alkyl$)$ radical; an N,N-di$(C_1-C_6)$ alkylcarbamyl$(C_1-C_6$ alkyl$)$ radical; a trifluoro$(C_1-C_6$ alkyl$)$ radical; an aminosulphonyl$(C_1-C_6$ alkyl$)$ radical; an N-Z-aminosulphonyl$(C_1-C_6$ alkyl$)$ radical; an N-($C_1$–$C_6$)alkylaminosulphonyl($C_1$–$C_6$ alkyl) radical; an N,N-di($C_1$–$C_6$)alkylaminosulphonyl($C_1$–$C_6$ alkyl) radical; a ($C_1$–$C_6$)alkylsulphinyl($C_1$–$C_6$ alkyl) radical; a ($C_1$–$C_6$)alkylsulphonyl($C_1$–$C_6$ alkyl) radical; a ($C_1$–$C_6$) alkylcarbonyl($C_1$–$C_6$ alkyl) radical; an amino($C_1$–$C_6$ alkyl) radical, wherein the alkyl is unsubstituted or substituted with at least one hydroxyl radical; an amino ($C_1$–$C_6$ alkyl) radical, wherein the alkyl is substituted with at least one hydroxyl radical and wherein the amine is substituted with one or two radicals, which radicals are identical or different, and are chosen from $C_1$–$C_6$ alkyl, monohydroxy($C_1$–$C_6$ alkyl), polyhydroxy($C_2$–$C_6$ alkyl), ($C_1$–$C_6$)alkylcarbonyl, formyl, trifluoro($C_1$–$C_6$) alkylcarbonyl, ($C_1$–$C_6$)alkylcarboxyl, carbamyl, N-($C_1$–$C_6$)alkylcarbamyl, N,N-di($C_1$–$C_6$)alkylcarbamyl, thiocarbamyl, and ($C_1$–$C_6$)alkylsulphonyl radicals, and from the group Z defined below, or which may form, together with the nitrogen atom to which they are attached, a 5- or 6-membered ring containing carbon or containing at least one heteroatom;

Z is chosen from the unsaturated cationic groups of formulae (II) and (III), and the saturated cationic groups of formula (IV):

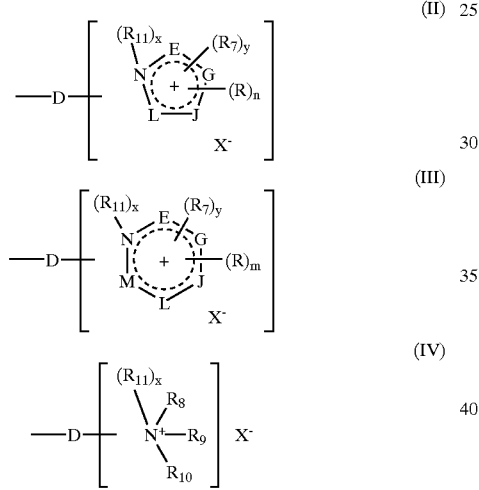

in which:

D is a linking arm chosen from linear and branched alkyl chains, which may be interrupted by at least one heteroatom such as oxygen, sulphur or nitrogen, and which may be substituted with at least one radical chosen from hydroxyl and $C_1$–$C_6$ alkoxy, and which may carry at least one ketone function; in one embodiment of the invention, the alkyl chains contain from 1 to 14 carbon atoms;

the members E, G, J, L and M, which are identical or different, are chosen from carbon, oxygen, sulphur and nitrogen atoms;

n is an integer ranging from 0 to 4;

m is an integer ranging from 0 to 5;

the radicals R, which are identical or different, are chosen from a group Z', which has the same definition as the group Z, and which definition is identical to or different from the group Z; a halogen atom; a hydroxyl radical; a $C_1$–$C_6$ alkyl radical; a monohydroxy($C_1$–$C_6$ alkyl) radical; a polyhydroxy($C_2$–$C_6$ alkyl) radical; a nitro radical; a cyano radical; a cyano($C_1$–$C_6$ alkyl) radical; a $C_1$–$C_6$ alkoxy radical; a tri($C_1$–$C_6$)alkylsilane($C_1$–$C_6$ alkyl) radical; an amido radical; an aldehydo radical; a carboxyl radical; a $C_1$–$C_6$ alkylcarbonyl radical; a thio radical; a thio($C_1$–$C_6$ alkyl) radical; a ($C_1$–$C_6$)alkylthio radical; an amino radical; an amino radical protected with a radical chosen from ($C_1$–$C_6$)alkylcarbonyl, carbamyl, and ($C_1$–$C_6$)alkylsulphonyl; a group NHR" and a group NR"R'", wherein R" and R'", which are identical or different, are chosen from a $C_1$–$C_6$ alkyl radical, a monohydroxy($C_1$–$C_6$ alkyl) radical, and a polyhydroxy($C_2$–$C_6$ alkyl) radical;

$R_7$ is chosen from a $C_1$–$C_6$ alkyl radical, a monohydroxy ($C_1$–$C_6$ alkyl) radical, a polyhydroxy($C_2$–$C_6$ alkyl) radical, a cyano($C_1$–$C_6$ alkyl) radical, a tri($C_1$–$C_6$) alkylsilane($C_1$–$C_6$ alkyl) radical, a ($C_1$–$C_6$)alkoxy ($C_1$–$C_6$ alkyl) radical, a carbamyl($C_1$–$C_6$ alkyl) radical, a ($C_1$–$C_6$)alkylcarboxy($C_1$–$C_6$ alkyl) radical, a benzyl radical, and a group Z', having the same definition as the group Z, and which definition is identical to or different from the group Z;

$R_8$, $R_9$ and $R_{10}$, which are identical or different, are chosen from a $C_1$–$C_6$ alkyl radical; a monohydroxy ($C_1$–$C_6$ alkyl) radical; a polyhydroxy($C_2$–$C_6$ alkyl) radical; a ($C_1$–$C_6$)alkoxy($C_1$–$C_6$ alkyl) radical; a cyano ($C_1$–$C_6$ alkyl) radical; an aryl radical; a benzyl radical; an amido($C_1$–$C_6$ alkyl) radical; a tri($C_1$–$C_6$)alkylsilane ($C_1$–$C_6$ alkyl) radical; and an amino($C_1$–$C_6$ alkyl) radical, wherein the amine is protected with a radical chosen from ($C_1$–$C_6$)alkylcarbonyl, carbamyl, and ($C_1$–$C_6$)alkylsulphonyl; two of the radicals $R_8$, $R_9$ and $R_{10}$ may also form, together with the nitrogen atom to which they are attached, a saturated 5- or 6-membered ring containing carbon or capable of containing at least one heteroatom such as, for example, a pyrrolidine ring, a piperidine ring, a piperazine ring or a morpholine ring, it being possible for the ring to be unsubstituted or substituted with a substituent chosen from a halogen atom, a hydroxyl radical, a $C_1$–$C_6$ alkyl radical, a monohydroxy($C_1$–$C_6$ alkyl) radical, a polyhydroxy($C_2$–$C_6$ alkyl) radical, a nitro radical, a cyano radical, a cyano($C_1$–$C_6$ alkyl) radical, a $C_1$–$C_6$ alkoxy radical, a tri($C_1$–$C_6$)alkylsilane($C_1$–$C_6$ alkyl) radical, an amido radical, an aldehydo radical, a carboxyl radical, a keto($C_1$–$C_6$ alkyl) radical, a thio radical, a thio($C_1$–$C_6$ alkyl) radical, a ($C_1$–$C_6$)alkylthio radical, an amino radical, or an amino radical protected with a radical chosen from ($C_1$–$C_6$)alkylcarbonyl, carbamyl, and ($C_1$–$C_6$)alkylsulphonyl; one of the radicals $R_8$, $R_9$ and $R_{10}$ may also be chosen from the group Z', having the same definition as the group Z, and which definition is identical or different from the group Z;

$R_{11}$ is chosen from a $C_1$–$C_6$ alkyl radical; a monohydroxy ($C_1$–$C_6$ alkyl) radical; a polyhydroxy($C_2$–$C_6$ alkyl) radical; an aryl radical; a benzyl radical; an amino ($C_1$–$C_6$ alkyl) radical, an amino($C_1$–$C_6$ alkyl) radical, wherein the amine is protected with a radical chosen from a ($C_1$–$C_6$)alkylcarbonyl, a carbamyl, and a ($C_1$–$C_6$)alkylsulphonyl; a carboxy($C_1$–$C_6$ alkyl) radical; a cyano($C_1$–$C_6$ alkyl) radical; a carbamyl($C_1$–$C_6$ alkyl) radical; a trifluoro($C_1$–$C_6$ alkyl) radical; a tri ($C_1$–$C_6$)alkylsilane($C_1$–$C_6$ alkyl) radical; a sulphonamido($C_1$–$C_6$ alkyl) radical; a ($C_1$–$C_6$) alkylcarboxy($C_1$–$C_6$ alkyl) radical; a ($C_1$–$C_6$) alkylsulphinyl($C_1$–$C_6$ alkyl) radical; a ($C_1$–$C_6$) alkylsulphonyl($C_1$–$C_6$ alkyl) radical; a ($C_1$–$C_6$) alkylketo($C_1$–$C_6$ alkyl) radical; an N-($C_1$–$C_6$) alkylcarbamyl($C_1$–$C_6$ alkyl) radical; and an N-($C_1$–$C_6$) alkylsulphonamido($C_1$–$C_6$ alkyl) radical;

x and y are the integers 0 or 1, with the following conditions:
in the unsaturated cationic groups of formula (II):
when x is 0, the linking arm D is attached to the nitrogen atom;
when x is 1, the linking arm D is attached to one of the members E, G, J or L;
y is 1:
1) when the members E, G, J and L are simultaneously a carbon atom, and $R_7$ is carried by the nitrogen atom of the unsaturated ring; or
2) when at least one of the members E, G, J and L is a nitrogen atom onto which the radical $R_7$ is attached;
in the unsaturated cationic groups of formula (III):
when x is 0, the linking arm D is attached to the nitrogen atom;
when x is 1, the linking arm D is attached to one of the members E, G, J, L or M;
y is 1 when at least one of the members E, G, J, L and M is a divalent atom, and $R_7$ is carried by the nitrogen atom of the unsaturated ring;
in the cationic groups of formula (IV):
if x is 0, then the linking arm D is attached to the nitrogen atom carrying the radicals $R_8$ to $R_{10}$;
if x is 1, then two of the radicals $R_8$ to $R_{10}$ conjointly form, with the nitrogen atom to which they are attached, a saturated 5- or 6-membered ring as defined above; and the linking arm D is carried by a carbon atom of the said saturated ring;

$X^-$ is chosen from monovalent and divalent anions; in one embodiment of the invention, $X^-$ is chosen from: (i) a halogen atom such as chlorine, bromine, fluorine, and iodine, (ii) a hydroxide, (iii) a hydrogen sulphate, and (iv) a ($C_1$–$C_6$)alkylsulphate such as, for example, methyl sulphates and ethyl sulphates;
it being understood that the number of unsaturated cationic groups Z of formula (II), in which at least one of the members E, G, J and L is a nitrogen atom, is at least equal to 1.

The compounds of formula (I) may be optionally salified with strong inorganic acids such as HCl, HBr, and $H_2SO_4$, or organic acids such as acetic, lactic, tartaric, citric, and succinic acids.

The alkyl and alkoxy radicals cited above in the formulae (I), (II), (III) and (IV) may be linear or branched.

Examples of rings of the unsaturated groups Z of formula (II) above, include the pyrrole, imidazole, pyrazole, oxazole, thiazole, and triazole rings.

The rings of the unsaturated groups Z of formula (III), above, may be, for example, pyridine, pyrimidine, pyrazine, oxazine, and triazine rings.

In one embodiment of the invention, the compounds of formula (I) are chosen from:

1-[2-(9,10-Dioxo-9,10-dihydroanthracen-1-ylamino)ethyl]-3-methyl-3H-imidazol-1-ium bromide,
1-Methyl-3-[3-(4-methylamino-9,10-dioxo-9,10-dihydroanthracen-1-ylamino)propyl]-3H-imidazol-1-ium hydrogen sulphate,
1-[2-(4-Hydroxy-9,10-dioxo-9,10-dihydroanthracen-1-ylamino)ethyl]-3-methyl-3H-imidazol-1-ium bromide,
1-[3-(9,10-Dioxo-9,10-dihydroanthracen-1-ylamino)propyl]-3-methyl-3H-imidazol-1-ium methosulphate,
1-[3-(4-Hydroxy-9,10-dioxo-9,10-dihydroanthracen-1-ylamino)propyl]-3-methyl-3H-imidazol-1-ium methosulphate,
1-{3-[4-(2-Hydroxyethylamino)-9,10-dioxo-9,10-dihydroanthracen-1-ylamino]propyl}-3-methyl-3H-imidazol-1-ium methosulphate,
1-{3-[4-(2,3-Dihydroxypropylamino)-9,10-dioxo-9,10-dihydroanthracen-1-ylamino]propyl}-3-methyl-3H-imidazol-1-ium methosulphate,
1,4-bis[3-(9,10-Dioxo-9,10-dihydroanthracen-1,4-diylamino)propyl]-3-methyl-3H-imidazol-1-ium dimethosulphate,
1-[2-(9,10-Dioxo-9,10-dihydroanthracen-2-ylamino)ethyl]-3-methyl-3H-imidazol-1-ium bromide,
1-[2-(9,10-Dioxo-9,10-dihydroanthracen-2-ylamino)ethyl]-2-methyl-3H-pyrazol-1-ium bromide,
1-[2-(9,10-Dioxo-9,10-dihydroanthracen-1-ylamino)ethyl]-2-methyl-3H-pyrazol-1-ium bromide,
1,5-bis[3-(9,10-Dioxo-9,10-dihydroanthracen-1,5-diylamino)propyl]-3-methyl-3H-imidazol-1-ium dimethosulphate,
1,8-bis[3-(9,10-Dioxo-9,10-dihydroanthracen-1,8-diylamino)propyl]-3-methyl-3H-imidazol-1-ium dimethosulphate,
1-[2-(5,8-Diamino-9,10-dioxo-9,10-dihydroanthracen-1-ylamino)ethyl]-3-methyl-3H-imidazol-1-ium bromide, and
1-[3-(5,8-Diamino-9,10-dioxo-9,10-dihydroanthracen-1-ylamino)propyl]-3-methyl-3H-imidazol-1-ium methosulphate.

The compounds of formula (I) in accordance with the invention may be easily obtained, according to methods well known in the state of the art for the production of quaternized amines, for example:
in a single step, by condensation of an anthraquinone containing a haloalkyl radical with a compound carrying a tertiary amine radical, or by condensation of an anthraquinone containing a tertiary amine radical with a compound carrying a haloalkyl radical; or
in two steps, by condensation of an anthraquinone containing a haloalkyl radical with a compound carrying a secondary amine, or by condensation of a halogenated or hydroxylated anthraquinone with an amino(disubstituted) alkylamine, followed by quaternization with an alkylating agent.

The quaternization step is generally, for the sake of convenience, the last step in the synthesis, but may occur earlier in the sequence of reactions leading to the preparation of the compounds of formula (I).

A subject of the invention is also dyeing compositions for keratinous materials, comprising, in a medium appropriate for dyeing, an effective quantity for dyeing keratinous materials of at least one cationic aminoanthraquinone of formula (I) defined above.

Another subject of the invention is direct dyeing compositions for human keratinous fibers, and in particular hair, comprising, in a medium appropriate for dyeing, an effective quantity for dyeing keratinous materials of at least one cationic aminoanthraquinone as defined above by formula (I).

Another subject of the invention is the use of the cationic aminoanthraquinones of formula (I), as direct dyes, in, or for the preparation of, dyeing compositions for keratinous materials, in particular for human keratinous fibers such as hair.

However other characteristics, aspects and advantages of the invention will emerge even more clearly on reading the description which follows, as well as the various concrete, but not at all limiting, examples intended to illustrate it.

In one embodiment of the dyeing composition in accordance with the invention, the amount of the at least one cationic aminoanthraquinone of formula (I) in the dyeing composition ranges from about 0.005 to about 12%, relative to the total weight of the dyeing composition. In another embodiment, the amount of the at least one cationic aminoanthraquinone ranges from about 0.05 to about 6% by weight, relative to the total weight of the composition.

In order to obtain a variety of colors, the dyeing composition according to the invention may also contain, in addition to the cationic aminoanthraquinones of formula (I), at least one additional direct dye that is conventionally used in the art. Examples of the at least one additional direct dye include:

- nitrobenzene dyes, such as nitrophenylenediamines, nitrodiphenylamines, nitroanilines, nitrophenol ethers, nitrophenols, and nitropyridines;
- anthraquinone dyes other than those of formula (I);
- mono- and diazo, triarylmethane, azine, acridine and xanthene dyes; and
- metal-containing dyes.

The total amount of all these other direct addition dyes in the dye composition according to the present invention may range from about 0.05 to about 10% by weight relative to the total weight of the dyeing composition.

The cationic aminoanthraquinones of formula (I) may also be incorporated into dyeing compositions for oxidation dyeing which contains oxidation bases and optionally couplers, to increase the shimmer of the shades obtained with the oxidation dyes.

The medium (or carrier) appropriate for dyeing is generally water or a mixture of water and at least one organic solvent for solubilizing the compounds which would not be sufficiently soluble in water. Examples of organic solvents include lower $C_1$–$C_4$ alkanols, such as ethanol and isopropanol; glycerol; glycols and glycol ethers, such as 2-butoxyethanol, propylene glycol, propylene glycol monomethyl ether; aromatic alcohols, such as benzyl alcohol or phenoxyethanol; and similar products and mixtures thereof.

In one embodiment of the invention, the solvents may be present in an amount ranging from approximately 1 to approximately 40% by weight relative to the total weight of the dyeing composition. In another embodiment of the invention, the amount of solvents ranges from approximately 5 to approximately 30% by weight, relative to the weight of the composition.

It is also possible to add to the composition according to the invention fatty amides such as mono- and diethanolamides of acids derived from copra, lauric acid and oleic acid, in amounts ranging from about 0.05 to about 10% by weight, relative to the weight of the composition.

It is also possible to add to the composition according to the invention well-known state of the art surfactants of the anionic, cationic, nonionic, amphoteric or zwitterionic type or mixtures thereof. In one embodiment of the invention, these surfactants can be present in the composition in an amount ranging from about 0.1 to about 50% by weight, relative to the total weight of the composition. In another embodiment of the invention, the amount of these surfactants ranges from about 1 to about 20% by weight, relative to the total weight of the composition.

It is also possible to use thickening agents in an amount ranging from about 0.2 to about 5% by weight, relative to the total weight of the composition.

The dyeing composition according to the invention may contain, in addition, various customary adjuvants, such as antioxidants, perfumes, sequestering agents, dispersing agents, hair conditioners, preservatives, and opacifying agents, as well as any other adjuvant normally used in dyeing keratinous materials.

Of course persons skilled in the art will be careful to choose the optional additional compounds mentioned above such that the advantageous properties intrinsically attached to the dyeing composition according to the invention are not, or not substantially adversely modified by the addition(s) envisaged.

The dyeing composition according to the invention may be formulated at acidic, neutral or alkaline pH, it being possible for the pH to vary, for example, from approximately 3 to approximately 12. In one embodiment of the invention, the pH varies from approximately 5 to approximately 11. The pH can be adjusted by means of previously well-known alkalinizing agents or acidifying agents or buffers.

Suitable alkalinizing agents include ammonium hydroxide, alkali metal carbonates, alkanolamines such as mono-, di- and triethanolamines as well as their derivatives, sodium and potassium hydroxides and the compounds of formula:

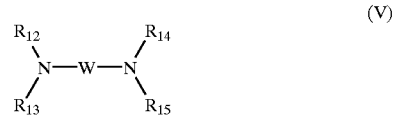

(V)

in which W is a propylene residue optionally substituted with a group chosen from a hydroxyl group and a $C_1$–$C_4$ alkyl radical; $R_{12}$, $R_{13}$, $R_{14}$ and $R_{15}$, simultaneously or independently of each other, are chosen from a hydrogen atom, a $C_1$–$C_6$ alkyl radical, and a hydroxy($C_1$–$C_6$ alkyl) radical.

The acidifying agents are conventionally inorganic or organic acids such as, for example, hydrochloric, tartaric, citric and phosphoric acids. An example of a buffer is potassium dihydrogen phosphate/sodium hydroxide.

The composition applied to the hair may be provided in various forms, such as in liquid, cream or gel form, or in any other form appropriate for dyeing keratinous fibers. In particular, it can be packaged under pressure in an aerosol can in the presence of a propellant and can form a foam.

Another subject of the present invention relates to a method of dyeing keratinous fibers, in particular human keratinous fibers such as hair, by direct dyeing, comprising allowing a dyeing composition containing at least one cationic aminoanthraquinone of formula (I) to act on dry or wet keratinous fibers. It is possible to use the composition according to the invention as a leave-in composition, that is to say that after applying the composition to the fibers, they are dried without intermediate rinsing.

In one embodiment, the process comprises allowing the composition to act on the fibers for an exposure time ranging from 3 to 60 minutes approximately, rinsing the fibers, optionally washing the fibers, and rinsing the fibers again and drying the fibers. In another embodiment of the invention, the process is similar to that just described, except that the exposure time ranges 5 to 45 minutes approximately.

Concrete and nonlimiting examples illustrating the invention will now be given.

EXAMPLES OF PREPARATION

Example 1

Preparation of 1-[2-(9,10-dioxo-9,10dihydroanthracen-1-ylamino)ethyl]-3-methyl-3H-imidazol-1-ium bromide, (Charge Delocalized in the Imidazole Ring)

16.5 g (0.05 mol) of 1-(2-bromoethylamino) anthraquinone (RN-3591-05-7) and 4.9 g (0.06 mol) of 1-methyl-1H-imidazole (RN-616-47-7) were suspended in 50 ml of toluene.

The mixture was then heated, with stirring, at the reflux temperature of toluene, for 4 hours (which corresponded with the disappearance of the starting anthraquinone in thin-layer chromatography) and then the boiling product was dewatered and it was washed twice in ethyl acetate.

After drying at 40° C. under vacuum, red crystals (19.2 g) were obtained, which melted with decomposition at 184–186° C. (Kofler).

The elemental analysis for $C_{20}H_{18}N_3O_2Br$ was:

| % | C | H | N | O | Br |
|---|---|---|---|---|---|
| theory | 58.27 | 4.40 | 10.19 | 7.79 | 19.38 |
| found | 58.26 | 4.42 | 10.04 | 7.85 | 19.26 |

Example 2

Preparation of 1-methyl-3-[3-(4-methylamino-9,10-dioxo-9,10dihydroanthracen-1-ylamino)propyl]-3H-imidazol-1-ium hydrogen sulphate, (Charge Delocalized in the Imidazole Ring)

In a first step, 1-(3-imidazolylpropylamino)-4-methylaminoanthraquinone was prepared by heating for 9 hours on a boiling waterbath and with stirring, the mixture comprising 47.4 g (0.15 mol) of 1-bromo-4-methylaminoanthraquinone (RN 128-93-8), 56.3 g (0.45 mol) of 3-imidazol-1-ylpropylamine (RN 5036-48-6) and 3.0 g of copper sulphate pentahydrate, in 60 ml of 1-methyl-2-pyrrolidone.

The mixture was then poured over 300 g of ice-cold water, the crystallized precipitate thus obtained was dewatered, the precipitate was made into a paste again in water and dried at 40° C. under vacuum over phosphoric anhydride.

45.1 g of dark blue crystals were obtained which, after purification by recrystallization from boiling 1,2-dimethoxyethane, melted at 140° C. (Kofler). The elemental analysis for $C_{21}H_{20}N_4O_2$ was:

| % | C | H | N | O |
|---|---|---|---|---|
| theory | 69.98 | 5.59 | 15.54 | 8.88 |
| found | 69.85 | 5.64 | 15.60 | 8.99 |

In a second step, and in order to quaternize the 1-(3-imidazolylpropylamino)-4-methylaminoanthraquinone obtained in the first step, 4.7 g (0.013 mol) of 1-(3-imidazolylpropylamino)-4-methylaminoanthraquinone and 1.37 ml (0.0143 mol) of dimethyl sulphate were suspended in 25 ml of chlorobenzene and the mixture was heated, with stirring, for 3 hours at 45° C.

The blue oil in suspension obtained was separated after settling out and washed several times in ethyl acetate and then dried under vacuum at 50° C.

3.8 g of a dark blue compound were obtained, which compound crystallized after purification and whose melting point (Kofler) was 192–194° C. The structure was in conformity in $^1H$ and $^{13}C$ NMR.

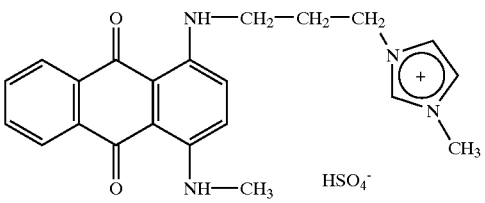

Examples of Dyeing Compositions

Example 3

The following dyeing composition was prepared:

| | |
|---|---|
| Aminoanthraquinone prepared in Example 1 ($10^{-3}$ mol) | 0.412 g |
| Benzyl alcohol | 4.0 g |
| Polyethylene glycol 6EO | 6.0 g |
| Hydroxyethylcellulose | 0.7 g |
| Alkylpolyglucoside in aqueous solution containing 60% A.M.* | 4.5 g A.M. |
| Phosphate buffer qs | pH 7 |
| Demineralized water qs | 100 g |

*Active material

The above composition was applied to locks of permanently waved or natural grey hair which was 90% white and allowed to act for 20 minutes. After rinsing with running water and drying, the hair was dyed in a copper-colored red shade.

Example 4

The following dyeing composition was prepared:

| | |
|---|---|
| Aminoanthraquinone prepared in Example 2 | 0.49 g |
| Oleic diethanolamide | 3 g |
| Lauric acid | 1 g |
| Ethylene glycol monoethyl ether | 5 g |
| Hydroxyethylcellulose | 2 g |
| 2-Amino-2-methyl-1-propanol qs | pH 9.5 |
| Demineralized water qs | 100 g |

The above composition was applied to locks of permanently waved or natural grey hair which was 90% white and allowed to act for 30 minutes. After rinsing with running water and drying, the hair was dyed an intense blue shade.

Comparative Example 5 and 6

In parallel with the composition of Example 3, two comparative compositions (3A) and (3B) were prepared which, as a replacement for the cationic aminoanthraquinone of the invention contained, in molar equivalent, two cationic aminoanthraquinones of the prior art described in French Patent No. 1,379,649, and in which the cationic charge was located on the nitrogen:

Comparative Composition (3A)
with:

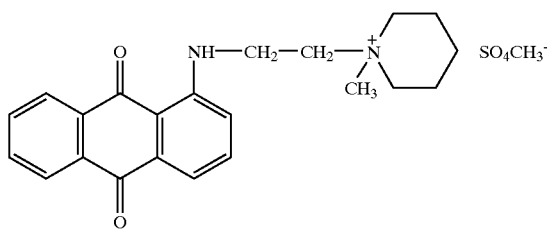

Comparative Composition (3B)
with

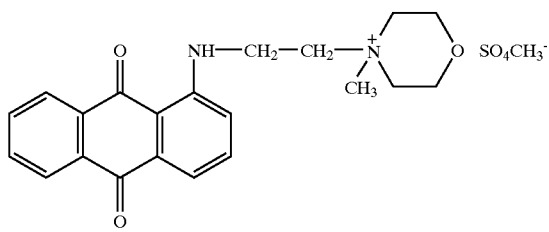

The other constituents of comparative compositions (3A) and (3B) were identical, in type and concentration, to those of composition 3 in accordance with the invention.

Locks of hair were then dyed with each of the comparative compositions (3A) and (3B) according to the same protocol and with the same hair quality as in Example 3.

The shades obtained with the aid of each of the three compositions and the shade of the non-dyed hair (control composition) were measured with a Minolta CM 2002 colorimeter and expressed as H, V, C, in the MUNSELL notation (ASTM D 1535-68 standard), H designating the shade or HUE, V designating the intensity or VALUE, and C the purity or CHROMATICITY.

These values, on the basis of permanently dyed hair, are presented in the following Table (I):

TABLE (I)

| COMPOSITIONS | H | V | C |
|---|---|---|---|
| (3) | 7.5R | 3.8 | 6.3 |
| (3A) | 8.6R | 3.7 | 6.3 |
| (3B) | 8.8R | 4.1 | 6.7 |
| Control | 4.0Y | 5.4 | 1.4 |

The locks dyed with the aid of each of the three compositions 3, (3A) and (3B) were then subjected to a light test (XENOTEST).

Description of the Test of Resistance to Light (Xenotest)

The dyed hairs are attached to a support (cardboard or plastic). These supports are placed on sample holders which rotate around a Xenon lamp for a period of 40 hours at a humidity level of 60% RH (Relative Humidity) and at a temperature of 25° C.

The shades of the locks which were subjected to a light test were then measured using the CM 2002 colorimeter and exhibited the following [combined in Table (11) below]:

TABLE (II)

| COMPOSITIONS | H | V | C |
|---|---|---|---|
| (3) | 9.1R | 3.9 | 5.9 |
| (3A) | 0.8YR | 4.1 | 5.5 |
| (3B) | 0.8YR | 4.2 | 5.6 |

The variation in color between the locks dyed before Xenotest and those dyed after Xenotest was quantified using the NICKERSON equation which defines the color variation indices: $I=(C/5)\times 2\Delta H+6\Delta V+3\Delta C$ (this equation being described in the publication: "Journal of the Optical Society of America", 1944-Sept-Vol34-No.9-p550–570), and the percentage deterioration of the shades, caused by the light test, was evaluated based on the equation $I_b/I_a\times 100$, $I_b$ defining the color variation index between the locks dyed after Xenotest and the locks dyed before Xenotest, $I_a$ defining the color variation index between the locks dyed before Xenotest and the control locks.

Thus, for each of the three shades obtained with the compositions 3, (3A) and (3B), the percentages of deterioration were the following:

| with composition 3 | 17.4% |
|---|---|
| with composition (3A) | 30.9% |
| with composition (3B) | 28.8%. |

Conclusion

The composition for direct dyeing comprising an aminoanthraquinone according to the present invention (composition 3) produced a shade which was more resistant to light than those obtained with the two compositions for direct dyeing comprising prior art aminoanthraquinones [compositions (3A) and (3B)]: only 17.4% of deterioration for the composition according to the present invention, compared with 30.9% and 28.8%, respectively for the two prior art compositions.

What is claimed is:

1. A cationic aminoanthraquinone of formula (I) or an acid-addition salt thereof:

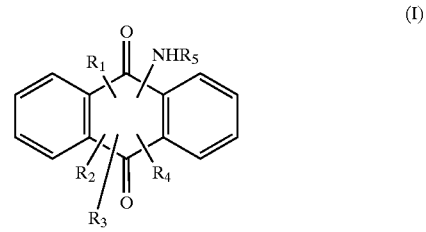

in which:

$R_1$, $R_2$, $R_3$ and $R_4$, which may be identical or different, are chosen from a hydrogen atom; a halogen atom; a group Z defined below; a ($C_1$–$C_6$)alkyl radical; a monohydroxy ($C_1$–$C_6$ alkyl) radical; a polyhydroxy($C_2$–$C_6$ alkyl) radical; a cyano radical; a nitro radical; a carboxyl radical; a carbamyl radical; a sulpho radical; an unsubstituted amino radical; a substituted amino radical $NHR'_5$, wherein $R'_5$ has the same definition as $R_5$ below, and wherein $R'_5$ may be identical to or different from $R_5$ below; and an $OR_6$ and $SR_6$ group, wherein $R_6$ is as defined below;

$R_5$ is chosen from a hydrogen atom; a group Z defined below; a $C_1$–$C_6$ alkyl radical; a monohydroxy($C_1$–$C_6$ alkyl) radical; a polyhydroxy($C_2$–$C_6$ alkyl) radical; a ($C_1$–$C_6$)alkoxy($C_1$–$C_6$ alkyl) radical; an aryl radical; a benzyl radical; a cyano($C_1$–$C_6$ alkyl) radical; a carbamyl ($C_1$–$C_6$ alkyl) radical; an N-($C_1$–$C_6$)alkylcarbamyl ($C_1$–$C_6$ alkyl) radical; an N,N-di($C_1$–$C_6$)alkylcarbamyl ($C_1$–$C_6$ alkyl) radical; a thiocarbamyl($C_1$–$C_6$ alkyl) radical; a trifluoro($C_1$–$C_6$ alkyl) radical; a sulpho($C_1$–$C_6$ alkyl) radical; a ($C_1$–$C_6$)alkylcarboxy($C_1$–$C_6$ alkyl) radical; a ($C_1$–$C_6$)alkylsulphinyl($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$)alkylaminosulphonyl($C_1$–$C_6$ alkyl) radical; an N,N-di($C_1$–$C_6$)alkylaminosulphonyl($C_1$–$C_6$ alkyl) radical; a ($C_1$–$C_6$)alkylcarbonyl($C_1$–$C_6$ alkyl) radical; an amino($C_1$–$C_6$ alkyl) radical, wherein the alkyl is unsubstituted or substituted with at least one hydroxyl radical; an amino($C_1$–$C_6$ alkyl) radical, wherein the alkyl is substituted with at least one hydroxyl radical and wherein the amine is substituted with one or two radicals, which are identical or different, and which are chosen from $C_1$–$C_6$ alkyl, monohydroxy($C_1$–$C_6$ alkyl), polyhydroxy($C_2$–$C_6$ alkyl), ($C_1$–$C_6$)alkylcarbonyl, carbamyl, N-($C_1$–$C_6$) alkylcarbamyl, N,N-di($C_1$–$C_6$)alkylcarbamyl, ($C_1$–$C_6$) alkylsulphonyl, formyl, trifluoro($C_1$–$C_6$)alkylcarbonyl, ($C_1$–$C_6$)alkylcarboxyl, thiocarbamyl, and a group Z defined below, or which may form, together with the nitrogen atom to which they are attached, a 5- or 6-membered ring containing atoms chosen from carbon and heteroatoms;

$R_6$ is chosen from a hydrogen atom; a $C_1$–$C_6$ alkyl radical; a monohydroxy($C_1$–$C_6$ alkyl) radical; a polyhydroxy ($C_2$–$C_6$ alkyl) radical; a group Z defined below; a ($C_1$–$C_6$) alkoxy($C_1$–$C_6$ alkyl) radical; an aryl radical; a benzyl radical; a carboxy($C_1$–$C_6$ alkyl) radical; a ($C_1$–$C_6$) alkylcarboxy($C_1$–$C_6$ alkyl) radical; a cyano($C_1$–$C_6$ alkyl) radical; a carbamyl($C_1$–$C_6$ alkyl) radical; an N-($C_1$–$C_6$) alkylcarbamyl($C_1$–$C_6$ alkyl) radical; an N,N-di($C_1$–$C_6$) alkylcarbamyl($C_1$–$C_6$ alkyl) radical; a trifluoro($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$)alkylaminosulphonyl($C_1$–$C_6$ alkyl) radical; an N,N-di($C_1$–$C_6$)alkylaminosulphonyl($C_1$–$C_6$ alkyl) radical; a ($C_1$–$C_6$)alkylsulphinyl($C_1$–$C_6$ alkyl) radical; a ($C_1$–$C_6$)alkylsulphonyl($C_1$–$C_6$ alkyl) radical; a ($C_1$–$C_6$) alkylcarbonyl($C_1$–$C_6$ alkyl) radical; an amino($C_1$–$C_6$ alkyl) radical, wherein the alkyl is unsubstituted or substituted with at least one hydroxyl radical; an amino ($C_1$–$C_6$ alkyl) radical, wherein the alkyl is substituted with at least one hydroxyl radical and wherein the amine is substituted with one or two radicals, which are identical or different, and which are chosen from $C_1$–$C_6$ alkyl, monohydroxy($C_1$–$C_6$ alkyl), polyhydroxy($C_2$–$C_6$ alkyl), ($C_1$–$C_6$)alkylcarbonyl, formyl, trifluoro($C_1$–$C_6$) alkylcarbonyl, ($C_1$–$C_6$)alkylcarboxyl, carbamyl, N-($C_1$–$C_6$)alkylcarbamyl, N,N-di($C_1$–$C_6$)alkylcarbamyl, thiocarbamyl, and ($C_1$–$C_6$)alkylsulphonyl radicals, and from a group Z defined below, or which may form, together with the nitrogen atom to which they are attached, a 5- or 6-membered ring containing atoms chosen from carbon and heteroatoms;

Z is chosen from the unsaturated cationic groups of formulae (II) and (III), and the saturated cationic groups of formula (IV):

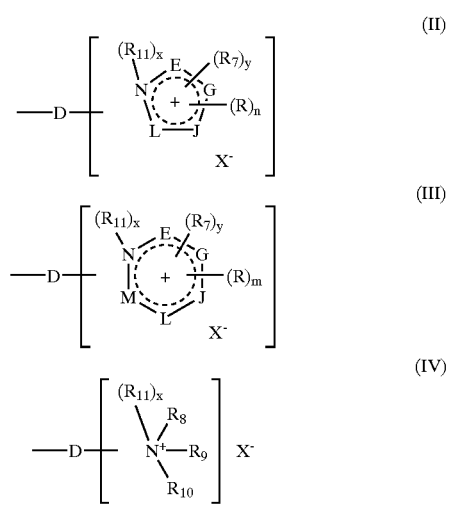

in which:

D is a linking arm which is chosen from linear and branched alkyl chains, which may be interrupted by at least one heteroatom, and which may be substituted with at least one radical chosen from a hydroxyl and a $C_1$–$C_6$ alkoxy, and which may carry at least one ketone function;

E, G, J, L and M, which are identical or different, are chosen from carbon, oxygen, sulphur, and nitrogen atoms;

n is an integer ranging from 0 to 4;

m is an integer ranging from 0 to 5;

the radicals R, which are identical or different, are chosen from a group Z', wherein Z' has the same definition as Z, and wherein the group Z' is identical or different from the group Z; a halogen atom; a hydroxyl radical; a $C_1$–$C_6$ alkyl radical; a monohydroxy($C_1$–$C_6$ alkyl) radical; a polyhydroxy($C_2$–$C_6$ alkyl) radical; a nitro radical; a cyano radical; a cyano($C_1$–$C_6$ alkyl) radical; a $C_1$–$C_6$ alkoxy radical; a tri($C_1$–$C_6$)alkylsilane($C_1$–$C_6$ alkyl) radical; an amido radical; an aldehydo radical; a carboxyl radical; a $C_1$–$C_6$ alkylcarbonyl radical; a thio radical; a thio($C_1$–$C_6$ alkyl) radical; a ($C_1$–$C_6$)alkylthio radical; an amino radical; an amino radical protected with a radical chosen from ($C_1$–$C_6$)alkylcarbonyl, carbamyl, and ($C_1$–$C_6$)alkylsulphonyl; and an NHR" and an NR"R'" group, wherein R" and R'", which are identical or different, are chosen from a $C_1$–$C_6$ alkyl radical, a monohydroxy($C_1$–$C_6$ alkyl) radical, and a polyhydroxy($C_2$–$C_6$ alkyl) radical;

$R_7$ is chosen from a $C_1$–$C_6$ alkyl radical; a monohydroxy ($C_1$–$C_6$ alkyl) radical; a polyhydroxy($C_2$–$C_6$ alkyl) radical; a cyano($C_1$–$C_6$ alkyl) radical; a tri($C_1$–$C_6$)alkylsilane ($C_1$–$C_6$ alkyl) radical; a ($C_1$–$C_6$)alkoxy($C_1$–$C_6$ alkyl) radical; a carbamyl($C_1$–$C_6$ alkyl) radical; a ($C_1$–$C_6$) alkylcarboxy($C_1$–$C_6$ alkyl) radical; a benzyl radical; and a group Z', wherein Z' has the same definition as Z, and wherein the group Z' is identical or different from the group Z;

$R_8$, $R_9$ and $R_{10}$, which are identical or different, are chosen from a $C_1$–$C_6$ alkyl radical; a monohydroxy($C_1$–$C_6$ alkyl) radical; a polyhydroxy($C_2$–$C_6$ alkyl) radical; a ($C_1$–$C_6$) alkoxy($C_1$–$C_6$ alkyl) radical; a cyano($C_1$–$C_6$ alkyl) radical; an aryl radical; a benzyl radical; an amido($C_1$–$C_6$ alkyl) radical; a tri($C_1$–$C_6$)alkylsilane($C_1$–$C_6$ alkyl) radical; and an amino($C_1$–$C_6$ alkyl) radical, wherein the amine is protected with a radical chosen from ($C_1$–$C_6$) alkylcarbonyl, carbamyl, and ($C_1$–$C_6$)alkylsulphonyl; two of the radicals $R_8$, $R_9$ and $R_{10}$ may also form, together with the nitrogen atom to which they are attached, a saturated 5- or 6-membered ring containing atoms selected from carbon and heteroatoms; one of the radicals $R_8$, $R_9$ and $R_{10}$ may also be chosen from a group Z', wherein Z' has the same definition as Z, and wherein the group Z' is identical or different from the group Z;

$R_{11}$ is chosen from a $C_1$–$C_6$ alkyl radical; a monohydroxy ($C_1$–$C_6$ alkyl) radical; a polyhydroxy($C_2$–$C_6$ alkyl) radical; an aryl radical; a benzyl radical; an amino ($C_1$–$C_6$ alkyl) radical; an amino($C_1$–$C_6$ alkyl) radical, wherein the amine is protected with a radical chosen from ($C_1$–$C_6$)alkylcarbonyl, carbamyl, and a ($C_1$–$C_6$) alkylsulphonyl radical; a carboxy($C_1$–$C_6$ alkyl) radical; a cyano($C_1$–$C_6$ alkyl) radical; a carbamyl($C_1$–$C_6$ alkyl) radical; a trifluoro($C_1$–$C_6$ alkyl) radical; a tri($C_1$–$C_6$) alkylsilane($C_1$–$C_6$ alkyl) radical; a sulphonamido ($C_1$–$C_6$ alkyl) radical; a ($C_1$–$C_6$)alkylcarboxy($C_1$–$C_6$ alkyl) radical; a ($C_1$–$C_6$)alkylsulphinyl($C_1$–$C_6$ alkyl) radical; a ($C_1$–$C_6$)alkylsulphonyl($C_1$–$C_6$ alkyl) radical; a ($C_1$–$C_6$)alkylketo($C_1$–$C_6$ alkyl) radical; an N-($C_1$–$C_6$) alkylcarbamyl($C_1$–$C_6$ alkyl) radical; and an N-($C_1$–$C_6$) alkylsulphonamido($C_1$–$C_6$ alkyl) radical;

x and y are integers equal to 0 or 1, with the following conditions:

in the unsaturated cationic groups of formula (II):
when x is 0, the linking arm D is attached to the nitrogen atom;
when x is 1, the linking arm D is attached to one of E, G, J or L;
y may only be 1:
1) when E, G, J and L are simultaneously a carbon atom, and the radical $R_7$ is carried by the nitrogen atom of the unsaturated ring; or
2) when at least one of E, G, J and L is a nitrogen atom onto which the radical $R_7$ is attached;

in the unsaturated cationic groups of formula (III):
when x is 0, the linking arm D is attached to the nitrogen atom;
when x is 1, the linking arm D is attached to one of E, G, J, L or M;
y may only take the value 1 when at least one of E, G, J, L and M is a divalent atom, and the radical $R_7$ is carried by the nitrogen atom of the unsaturated ring;

in the cationic groups of formula (IV):
when x is 0, then the linking arm D is attached to the nitrogen atom carrying the radicals $R_8$ to $R_{10}$;
when x is 1, then two of the radicals $R_8$ to $R_{10}$ conjointly form, with the nitrogen atom to which they are attached, a saturated 5- or 6-membered ring as defined above and the linking arm D is carried by a carbon atom of the saturated ring;

X is chosen from monovalent and divalent anions; it being understood that: the number of unsaturated cationic groups Z of formula (II), in which at least one of E, G, J and L is a nitrogen atom is at least equal to 1.

2. A cationic aminoanthraquinone or an acid-addition salt thereof according to claim 1, wherein D is chosen from linear and branched alkyl chains containing from 1 to 14 carbon atoms.

3. A cationic aminoanthraquinone or an acid-addition salt thereof according to claim 1, wherein the at least one heteroatom which may interrupt the alkyl chains of the linking arm D is chosen from oxygen, sulphur, and nitrogen.

4. A cationic aminoanthraquinone or an acid-addition salt thereof according to claim 1, wherein the 5- or 6-membered ring formed from two of the radicals $R_8$, $R_9$, and $R_{10}$, together with the nitrogen to which they are attached, is chosen from a pyrrolidine ring, a piperidine ring, a piperazine ring, and a morpholine ring, and wherein said rings are unsubstituted or substituted with a halogen atom, a hydroxyl radical, a $C_1$–$C_6$ alkyl radical, a monohydroxy($C_1$–$C_6$ alkyl) radical, a polyhydroxy($C_2$–$C_6$ alkyl) radical, a nitro radical, a cyano radical, a cyano($C_1$–$C_6$ alkyl) radical, a $C_1$–$C_6$ alkoxy radical, a tri($C_1$–$C_6$)alkylsilane($C_1$–$C_6$ alkyl) radical, an amido radical, an aldehydo radical, a carboxyl radical, a keto($C_1$–$C_6$ alkyl) radical, a thio radical, a thio($C_1$–$C_6$ alkyl) radical, a ($C_1$–$C_6$) alkylthio radical, an amino radical, and an amino radical protected with a radical chosen from ($C_1$–$C_6$) alkylcarbonyl, carbamyl, and ($C_1$–$C_6$)alkylsulphonyl.

5. A cationic aminoanthraquinone or an acid-addition salt thereof according to claim 1, wherein the rings of the unsaturated groups Z of formula (II) are chosen from pyrrole, imidazole, pyrazole, oxazole, thiazole and triazole rings.

6. A cationic aminoanthraquinone or an acid-addition salt thereof according to claim 1, wherein the rings of the unsaturated groups Z of formula (III) are chosen from pyridine, pyrimidine, pyrazine, oxazine and triazine rings.

7. A cationic aminoanthraquinone or an acid-addition salt thereof according to claim 1, wherein in formula (IV), two of the radicals $R_8$, $R_9$ and $R_{10}$ form a ring chosen from pyrrolidine, piperidine, piperazine, and morpholine, wherein said ring is unsubstituted or substituted with a substituent chosen from a halogen atom, a hydroxyl radical, a $C_1$–$C_6$ alkyl radical, a monohydroxy($C_1$–$C_6$ alkyl) radical, a polyhydroxy($C_2$–$C_6$ alkyl) radical, a nitro radical, a cyano radical, a cyano($C_1$–$C_6$ alkyl) radical, a $C_1$–$C_6$ alkoxy radical, a tri($C_1$–$C_6$)alkylsilane($C_1$–$C_6$ alkyl) radical, an amido radical, an aldehydo radical, a carboxyl radical, a ($C_1$–$C_6$ alkyl)carbonyl radical, a thio radical, a thio($C_1$–$C_6$ alkyl) radical, a ($C_1$–$C_6$)alkylthio radical, an amino radical, and an amino radical protected with a radical chosen from ($C_1$–$C_6$)alkylcarbonyl, carbamyl, and ($C_1$–$C_6$) alkylsulphonyl.

8. A cationic aminoanthraquinone or an acid-addition salt thereof according to claim 1, wherein said X⁻ is chosen from a halogen atom, a hydroxide, a hydrogen sulphate and a ($C_1$–$C_6$)alkyl sulphate.

9. A cationic aminoanthraquinone or an acid-addition salt thereof according to claim 1, wherein said cationic aminoanthraquinone is:

1-[2-(9,10-Dioxo-9,10-dihydroanthracen-1-ylamino)ethyl]-3-methyl-3H-imidazol-1-ium bromide, 1-Methyl-3-[3-(4-methylamino-9,10-dioxo-9,10-dihydroanthracen-1-ylamino)propyl]-3H-imidazol-1-ium hydrogen sulphate, 1-[2-(4-Hydroxy-9,10-dioxo-9,10-dihydroanthracen-1-ylamino)ethyl]-3-methyl-3H-imidazol-1-ium bromide, 1-[3-(9,10-Dioxo-9,10-dihydroanthracen-1-ylamino)propyl]-3-methyl-3H-imidazol-1-ium methosulphate, 1-[3-(4-Hydroxy-9,10-dioxo-9,10-dihydroanthracen-1-ylamino)propyl]-3-methyl-3H-imidazol-1-ium methosulphate, 1-{3-[4-(2-Hydroxyethylamino)-9,10-dioxo-9,10-dihydroanthracen-1-ylamino]propyl}-3-methyl-3H-imidazol-1-ium methosulphate, 1-{3-[4-(2,3-Dihydroxypropylamino)-9,10-dioxo-9,10-dihydroanthracen-1-ylamino]propyl}-3-methyl-3H-imidazol-1-ium methosulphate, 1,4-bis[3-(9,10-Dioxo-9,10-dihydroanthracen-1,4-diylamino)propyl]-3-methyl-3H-imidazol-1-ium dimethosulphate, 1-[2-(9,10-Dioxo-9,10-dihydroanthracen-2-ylamino)ethyl]-3-methyl-3H-imidazol-1-ium bromide, 1-[2-(9,10-Dioxo-9,10-dihydroanthracen-2-ylamino)ethyl]-2-methyl-3H-pyrazol-1-ium bromide, 1-[2-(9,10-Dioxo-9,10-dihydroanthracen-1-ylamino)ethyl]-2-methyl-3H-pyrazol-1-ium bromide, 1,5-bis[3-(9,10-Dioxo-9,10-dihydroanthracen-1,5-diylamino)propyl]-3-methyl-3H-imidazol-1-ium dimethosulphate, 1,8-bis[3-(9,10-Dioxo-9,10-dihydroanthracen-1,8-diylamino)propyl]-3-methyl-3H-imidazol-1-ium dimethosulphate, 1-[2-(5,8-Diamino-9,10-dioxo-9,10-dihydroanthracen-1-ylamino)ethyl]-3-methyl-3H-imidazol-1-ium bromide, or 1-[3-(5,8-Diamino-9,10-dioxo-9,10-dihydroanthracen-1-ylamino)propyl]-3-methyl-3H-imidazol-1-ium methosulphate.

10. A cationic aminoanthraquinone or an acid-addition salt thereof according to claim 1, wherein said acid-addition salt is chosen from hydrochlorides, hydrobromides, sulphates, citrates, succinates, tartrates, lactates, and acetates.

* * * * *

UNITED STATES PATENT AND TRADEMARK OFFICE
CERTIFICATE OF CORRECTION

PATENT NO. : 6,437,149 B1  
DATED : August 20, 2002  
INVENTOR(S) : Genet et al.

It is certified that error appears in the above-identified patent and that said Letters Patent is hereby corrected as shown below:

<u>Column 15,</u>  
Line 56, "X is" should read -- $X^-$ is --.

Signed and Sealed this

Fifteenth Day of October, 2002

Attest:

Attesting Officer

JAMES E. ROGAN  
*Director of the United States Patent and Trademark Office*